United States Patent [19]

Halperin et al.

[11] Patent Number: 5,358,959
[45] Date of Patent: Oct. 25, 1994

[54] METHODS FOR TREATING ARTERIOSCLEROSIS

[75] Inventors: Jose Halperin, Brookline; Carlo Brugnara, Newton Highlands, both of Mass.

[73] Assignee: President and Fellows of Harvard University, Cambridge, Mass.

[21] Appl. No.: 18,835

[22] Filed: Feb. 18, 1993

[51] Int. Cl.$^5$ .................................. A61K 31/415
[52] U.S. Cl. ................................ 514/396; 514/399; 514/824
[58] Field of Search ................ 514/396, 399, 824

[56] References Cited

U.S. PATENT DOCUMENTS

| | | | |
|---|---|---|---|
| 4,916,118 | 4/1990 | Fidler et al. | 514/16 |
| 5,132,315 | 7/1992 | Kohn et al. | 514/359 |

FOREIGN PATENT DOCUMENTS

WO/9119707  12/1991  PCT Int'l Appl.

OTHER PUBLICATIONS

Crimson Language Services No. 162–Dutch Patent, Pharmaceutical Preparation and Pharmaceutical Set for the Treatment of Cancer.
Forgue–Lafitte et al., Cancer Research 52, p. 6827–6831, Dec. 1992.
Teanakakis et al., Cancer 65, pp. 446–451, 1990.
Nardone et al., J. of Surg. Res. 44, pp. 425–429, 1988.

*Primary Examiner*—Marianne M. Cintins
*Assistant Examiner*—Kimberly R. Jordan
*Attorney, Agent, or Firm*—Wolf, Greenfield & Sacks

[57] ABSTRACT

The applicant has identified a particular class of imidazoles that inhibit endothelial cell, vascular smooth muscle cell and fibroblast proliferation. These imidazoles can be used to beneficially treat a variety of arteriosclerotic conditions.

21 Claims, 3 Drawing Sheets

METHODS FOR TREATING ARTERIOSCLEROSIS

FIELD OF THE INVENTION

The invention relates in general to the field of arteriosclerosis and more particularly to the use of imidazoles that inhibit the $Ca^{++}$ activated potassium channel in arresting endothelial cell, smooth muscle cell and fibroblast proliferation.

BACKGROUND OF THE INVENTION

Arteriosclerosis is a term used to describe a thickening and hardening of the arterial wall. It is believed to be responsible for the majority of deaths in the United States and in most westernized societies. Atherosclerosis is one type of arteriosclerosis that is believed to be the cause of most coronary artery disease, aortic aneurysm and arterial disease of the lower extremities, as well as contributing to cerebrovascular disease. Atherosclerosis is the leading cause of death in the United States.

A normal artery typically is lined on its inner-side only by a single layer of endothelial cells, the intima. The intima overlays the media, which contains only a single cell type, the smooth muscle cell. The outer-most layer of the artery is the adventitia. With aging, there is a continuous increase in the thickness of the intima, believed to result in part from migration and proliferation of smooth muscle cells from the media. A similar increase in the thickness of the intima also occurs as a result of various traumatic events or interventions, such as occurs when a balloon dilatation procedure causes injury to the vessel wall. To date, there is no proven treatment for atherosclerosis.

Imidazoles are synthetic antifungal agents that are used both topically and systemically. Indications for their use include ringworm, tinea versicolor and mucocutaneous candidiasis. These compounds are believed to act by inhibiting ergosterol synthesis in the fungal cell wall, and when given topically, may cause direct damage to the cytoplasmic membrane.

The fungi comprise five widely differing classes of primitive flora, and the variation in cell physiology and biochemistry are extreme. As a result, most antifungal agents have a very narrow spectrum of antifungal activity.

Various imidazoles have been suggested as treatments for prostate cancer. The only one known to the applicants to have been tested, ketoconazole, appears to inhibit, in high doses, testicular and adrenal synthesis of steroid hormones, including testosterone. The ability of ketoconazole to block steroid synthesis is effective in treating some prostate cancers because proliferation of certain prostate cancer cells is highly dependent upon testosterone. Thus, ketoconazole has been used as a hormonal adjuvant for prostate cancer treatment, it reduces plasma testosterone to castration levels. Ketoconazole, as will be described below, is not useful for inhibiting endothelial or smooth muscle cell proliferation.

SUMMARY OF THE INVENTION

The applicants have identified a particular class of imidazoles that inhibit endothelial and/or vascular smooth muscle cell proliferation. The applicants also have identified imidazoles that inhibit proliferation of fibroblasts. These imidazoles can be used to beneficially treat a variety of arteriosclerotic conditions and other conditions characterized by complications involving fibrosis, as described below.

According to one aspect of the invention, a method for treating an arteriosclerotic condition is provided. An imidazole is administered to a subject in need of such treatment. The imidazole is an inhibitor of the $Ca^{++}$ activated potassium channel and is an inhibitor of endothelial and vascular smooth muscle cell proliferation. The methods are particularly useful for subjects who have sustained an injury to a blood vessel. Preferred imidazoles are clotrimazole, miconazole and econazole.

According to another aspect of the invention, a method for inhibiting endothelial and vascular smooth muscle cell proliferation is provided. It involves the treatment of endothelial cells or vascular smooth muscle cells of a species with the imidazoles described above. The imidazoles inhibit the $Ca^{++}$ activated potassium channel of erythrocytes of the species. Such methods may be in vivo or ex vivo.

Likewise, methods for treating medical conditions involving fibrosis and for inhibiting the growth of fibroblasts are provided. Such methods involve contacting cells, tissues or subjects with imidazoles that inhibit the $Ca^{++}$ activated potassium channel.

Preferably the cells are in a preparation or in a tissue that is substantially free of fungi. As such, the treatment typically is for cells, tissues or subjects that are otherwise free of indications for the preferred imidazoles.

DETAILED DESCRIPTION OF THE PREFERRED EMBODIMENTS

Figure 1:
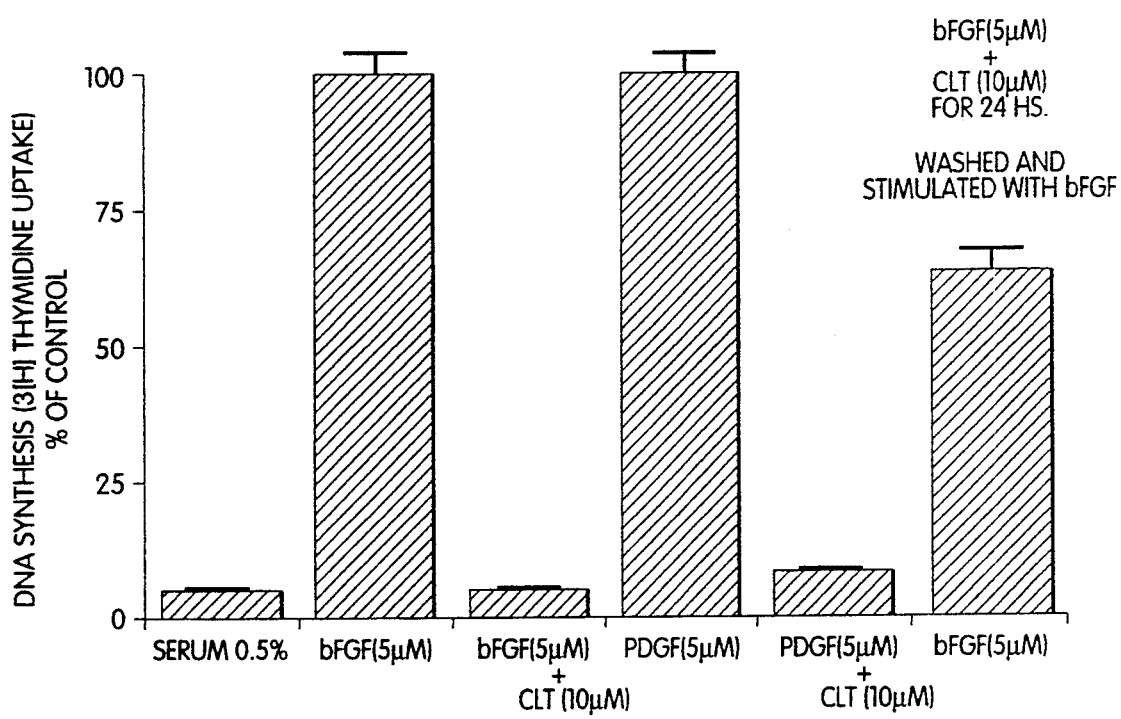
FIG. 1 is a graph illustrating the ability of clotrimazole to inhibit cell proliferation in vascular smooth muscle cells, and the ability to reverse the effects of clotrimazole treatment.

The invention is used in connection with treating arteriosclerotic conditions. An arteriosclerotic condition as used herein means classical atherosclerosis, accelerated atherosclerosis, atherosclerosis lesions and any other arteriosclerotic conditions characterized by undesirable endothelial and/or vascular smooth muscle cell proliferation, including vascular complications of diabetes.

Proliferation of vascular smooth muscle cells is a main pathological feature in classical atherosclerosis. Liberation of growth factors from endothelial cells, it is believed, stimulates the proliferation of subintimal smooth muscle which, in turn, reduces the caliber and finally obstructs the artery. The invention is useful in inhibiting such proliferation and, therefore, in delaying the onset of, inhibiting the progression of or even halting the progression of such proliferation and the associated atherosclerotic condition.

Proliferation of vascular smooth muscle cells produces accelerated atherosclerosis which is the main reason for failure of heart transplants that are not rejected. This proliferation also is believed to be mediated by growth factors and can result ultimately in obstruction of the coronary arteries. The invention is useful in inhibiting such obstruction and reducing the risk of or even preventing such failures.

Vascular injury also can result in endothelial and vascular smooth muscle cell proliferation. The injury can be caused by any number of traumatic events, or interventions, including vascular surgery and angioplasty procedures performed for example by balloon dilatation catheters. Re-stenosis is the main complication of successful balloon angioplasties of the coronary arteries. It is believed to be caused by the release of growth factors as a result of mechanically injuring the endothelial cells lining the coronary arteries. The invention can be useful in inhibiting unwanted endothelial and smooth muscle cell proliferation and delaying or even avoiding altogether re-stenosis.

Other arteriosclerotic conditions include diseases of the arterial wall that include proliferation of endothelial and/or vascular smooth muscle cells, such as vascular complications of diabetes, diabetic glomerulosclerosis and diabetes retinopathy.

Other uses of the invention include by-pass surgery, coronary by-pass surgery, and procedures in addition to balloon angioplasty for re-establishing patency in occluded or partly occluded vessels, e.g. atherectomy, laser procedures and ultrasonic procedures.

The invention also is useful in treating fibrosis and other medical complications of fibrosis, all resulting in whole or in part from the proliferation of fibroblasts. Medical conditions other than atherosclerosis include undesirable tissue adhesion resulting from surgery or injury.

The invention is used in connection with treating subjects having, suspected of having, developing or suspected developing such conditions.

A subject as used herein means humans, primates, horses, cows, pigs, sheep, goats, dogs, cats and rodents.

The compounds useful in the present invention are imidazoles that inhibit Ca++ activated potassium channel. Such imidazoles are either known to those of ordinary skill in the art or can be identified without undue experimentation using established tests routinely employed by those of ordinary skill in the art. One such test involves human erythrocytes and is described in the examples, below. When using this test, it is desirable to select imidazoles that are inhibitory to an extent of at least about 75%.

The imidazoles useful in the invention also inhibit endothelial and/or vascular smooth muscle cell proliferation. Imidazoles useful in the invention also inhibit the proliferation of fibroblasts. Inhibition of such proliferation may be tested without undue experimentation using established tests routinely employed be those of ordinary skill in the art (See e.g. below.) The imidazoles used in the methods of this invention preferably are inhibitory of endothelial and/or vascular smooth muscle cell proliferation in such tests to an extent of at least about 75%.

It was not expected that inhibitors of the Ca++ activated potassium channel would inhibit endothelial cell, vascular smooth muscle cell, or fibroblast proliferation. Other specific inhibitors of the Ca++ activated potassium channel (such as charybdotoxin, caliotoxin and iberotoxin) do not inhibit proliferation of endothelial or vascular smooth muscle cells. Moreover, inhibitors of other transport systems that are activated by mitogens, such as ouabain (highly specific inhibitor of the Na/K pump) and amiloride (inhibitor of Na/H exchange) do not inhibit cell proliferation. Thus, the results obtained by the inventor are surprising.

Without limiting the invention to the use of the specific compounds listed, the following is a list of preferred compounds and salts thereof useful in the methods of the invention.

Clotrimazole
1H-Imidazole,1-[(2-chlorophenyl)diphenylmethyl]-,
Lotrimin (Schering); Mycelex (Miles)

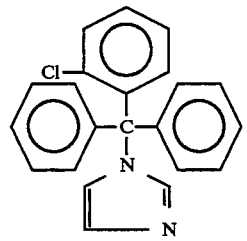

1-(o-Chloro-α,α-diphenylbenzyl)imidazole [23593-75-1]
$C_{22}H_{17}ClN_2$(344.84).

Econazole
1H-Imidazole,(±)-1-[2-[(4-chlorophenyl)methoxy]-2-(2,4-wdichlorophenyl)ethyl]-, mononitrate, Ecostatin (Squibb)

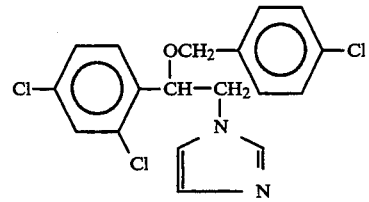

(±)-1-]2,4-Dichloro-β-[(p-chlorobenzyl)oxy]phenethyl]imidazole
mononitrate [68797-31-9]$C_{18}H_{15}Cl_3N_2O$.

Econazole Nitrate
1H-Imidazole, (±)-1-[2-[(4-chlorophenyl)methoxy]-2-(2,4-dichlorophenyl)ethyl]-, mononitrate, Ecostatin (Squibb)

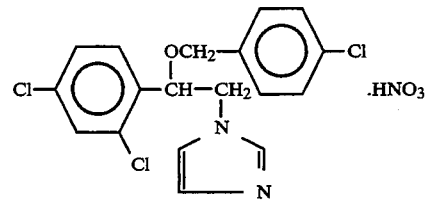

(±)-1-[2,4-Dichloro-β-[(p-chlorobenzyl)oxy]phenethyl]imidazole
mononitrate [68797-31-9]$C_{18}H_{15}Cl_3N_2O.HNO_3$ (440.70).

Miconazole
1H-Imidazole, 1-[2-(2,4-dichlorophenyl)-2-[(2,4-dichlorophenyl)methoxy]ethyl]-, Monistat (Janssen)

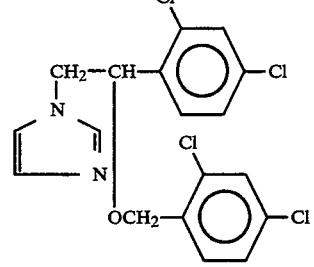

1-[2,4-Dichloro-β-[(2,4-dichlorobenzyl)oxy]phenethyl[imidazole
[22916-47-8]$C_{18}H_{14}Cl_4N_2O$ (416.12).

Miconazole Nitrate

-continued

Monistat (Ortho)

[22832-87-7] $C_{18}H_{14}Cl_4N_2O \cdot HNO_3$ (479.15).

The above imidazoles are well recognized, pharmacologically characterized, and licensed for use by the FDA today either as antimycotic agents or antiprotozoal agents. As such, established and empirically documented paremeters regarding their limited toxicity and their useful dosages are well described in the scientific and medical literature.

The imidazole used in the methods of the invention may be administered per se (neat) or in the form of a pharmaceutically acceptable salt. When used in medicine, the salts should be both pharmacologically and pharmaceutically acceptable, but non-pharmaceutically acceptable salts may conveniently be used to prepare the free active compound or pharmaceutically acceptable salts thereof. Pharmacologically and pharmaceutically acceptable salts include, but are not limited to, those prepared from the following acids: hydrochloric, hydrobromic, sulphuric, nitric, phosphoric, maleic, acetic, salicyclic, p-toluenesulfonic, tartaric, citric, methanesulphonic, formic, malonic, succinic, naphthalene-2-sulphonic, and benzenesulphonic. Also, pharmaceutically acceptable salts can be prepared as alkaline metal or alkaline earth salts, such as sodium, potassium or calcium salts of the carboxylic acid group. Thus, the present invention involves the use of pharmaceutical formulations which comprise certain imidazoles together with one or more pharmaceutically acceptable carriers and optionally other therapeutic ingredients. The carrier(s) and other ingredients of course must be pharmaceutically acceptable.

Analogs of the foregoing compounds that act as functional equivalents also are intended to be embraced as equivalents and within the scope of the invention.

A variety of administration routes are available. The particular mode selected will depend, of course, upon the particular drug selected, the particular condition being treated and the dosage required for therapeutic efficacy. The methods of this invention, generally speaking, may be practiced using any mode of administration that is medically acceptable, meaning any mode that produces therapeutic levels of the imidazoles of the invention without causing clinically unacceptable adverse effects. Such modes of administration include oral, rectal, topical, nasal, transdermal or parenteral (e.g. subcutaneous, intramuscular and intravenous) routes. Formulations for oral administration include discrete units such as capsules, tablets, lozenges and the like. Other routes include intrathecal administration directly into spinal fluid, direct introduction onto an arterial surface such as by various catheter and balloon angioplasty devices well known to those of ordinary skill in the art, and intraparenchymal injection into targeted areas on an organ such as a heart.

The compositions may conveniently be presented in unit dosage form and may be prepared by any of the methods well known in the art of pharmacy. Such methods include the step of bringing the active imidazole into association with a carrier which constitutes one or more accessory ingredients. In general, the compositions are prepared by uniformly and intimately bringing the imidazole into association with a liquid carrier, a finely divided solid carrier, or both, and then, if necessary, shaping the product.

Compositions of the present invention suitable for oral administration may be presented as discrete units such as capsules, cachets, tablets or lozenges, each containing a predetermined amount of the imidazole, in liposomes or as a suspension in an aqueous liquor or non-aqueous liquid such as a syrup, an elixir, or an emulsion.

Compositions suitable for parenteral administration conveniently comprise a sterile aqueous preparation of the imidazole, which is preferably isotonic with the blood of the recipient. This aqueous preparation may be formulated according to known methods using those suitable dispersing or wetting agents and suspending agents. The sterile injectable preparation may also be a sterile injectable solution or suspension in a non-toxic parenterally-acceptable diluent or solvent, for example as a solution in polyethylene glycol and lactic acid. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectibles.

Other delivery systems can include sustained release delivery systems. Preferred sustained release delivery systems are those which can provide for release of the imidazoles of the invention in sustained release pellets or capsules. Many types of sustained release delivery systems are available. These include, but are not limited to: (a) erosional systems in which the imidazole is contained in a form within a matrix, found in U.S. Pat. Nos. 4,452,775 (Kent), 4,667,014 (Nestor et al.) and 4,748,024 and 5,239,660 (Leonard) and (b) diffusional systems in which an active component permeates at a controlled rate through a polymer, found in U.S. Pat. Nos. 3,832,252 (Higuchi et al.) and 3,854,480 (Zaffaroni). In addition, a pump-based hardware delivery system can be used, some of which are adapted for implantation.

Oral administration for many arteriosclerotic conditions will be preferred because of the convenience to the patient, although topical and localized sustained delivery may be even more desirable for certain treatment regimens.

The imidazoles, when used in vivo, are administered in therapeutically effective amounts. A therapeutically effective amount means that amount necessary to delay the onset of, inhibit the progression of or halt altogether the onset or progression of the particular condition being treated. Such amounts will depend, of course, on the particular condition being treated, the severity of the condition, and individual patient parameters including age, physical condition, size, weight and concurrent treatment. These factors are well known to those of ordinary skill in the art and can be addressed with no more than routine experimentation. It is preferred generally that a maximum dose be used, that is, the highest safe does according to sound medical judgment. It will be understood by those of ordinary skill in the art, however, that a patient may insist upon a lower dose or tolerable dose for medical reasons, psychological reasons or for virtually any other reasons.

Generally, daily oral doses of active compound will be from about 0.01 milligrams/kg per day to 1000 milligrams/kg per day. Small does (0.01–1 mg) may be administered initially, followed by increasing doses up to about 1000 mg/kg per day. In the event that the antiarteriosclerotic response in a subject is insufficient at such doses, even higher doses (or effective higher doses by a different, more localized delivery route) may be employed to the extent patient tolerance permits. Multiple doses per day are contemplated to achieve appropriate systemic levels of compounds.

EXAMPLES

Materials

Abbreviations: ChTX, Charybdotoxin; CLT, clotrimazole; ECZ, econazole; MCZ, miconazole; FCZ, fluoconazole; METZ, metronidazole; IbTX, iberotoxin; KTX, kaliotoxin; DIDS, di-isothiocyano-disulfonyl stilbene; hemoglobin concentration; MCHC, mean corpuscular hemoglobin concentration; MOPS, 3-[N-morpholino]propanesulfonic acid.

Drugs and Chemicals

Synthetic charybdotoxin (ChTX) was purchased from Peptides International (Louisville, Ky.). A23187 was purchased from Calbiochem-Behring (LaJolla, Calif.). Fluconazole was provided by Pfizer Inc., Groton, Conn., disulfonic acid (MOPS), clotrimazole (CLT), miconazole, econazole, metronidazole, and all other drugs and chemicals were purchased from Sigma Chemical Co. (St. Louis, Mo.) and Fisher Scientific Co. (Fair Lawn, N.J.), and the radioisotope 86Rb from Dupont (Billerica, Mass.)

Assays for Cell Proliferation

DNA synthesis assessed by the uptake of [3H]thymidine: Cells are grown in either 48 or 96 wells plates (Costar, Cambridge, Mass.) at $10^4$ and 0.8 $10^3$ cells per well, respectively, and grown in Dubelcco's modified Eagle's medium (DME, Gibco, Grand Island, N.Y.) supplemented with 10% heat-inactivated calf serum; they are kept at 37° C. in 5% $CO_2$. When they reach confluence, usually between 3 and 4 days, the medium is replaced with DME 0.5% serum to make them quiescent, and mitogenesis assays are performed 24 hours later.

Quiescent cells are exposed to a mitogenic stimulus, such as 10% serum, PDGF (Sigma Co. St. Louis, Mo.), bFGF (Upstate Biotechnologies, Lake Placid, N.Y.), or other appropriate mitogen according to the cell line, and 3 hours 1 later μCi/ml of [3H]thymidine (Dupont, Billerica, Mass.) is added to the wells, and the cells maintained at 37° C./5% CO2 for additional 21 hours. Then the cells are washed 3 times with DME medium and the acid-precipitable radioactivity is extracted with cold 10% TCA (Sigma, Co). After neutralization with 0.3N NaOH (Sigma Co.), aliquots are counted in a Packard Tri-Carb Scintillation counter (Packard Instrument, Downer's Grove, Ill.).

Measurement of cell density in culture plates: Cells of a specific test cell line are seeded at precisely the same low density in culture plates and incubated for approximately 12 hours in DME 10% serum, or other culture medium depending on the cell line tested. After 12 hours, the test drug, for example clotrimazole 10 μM, is added to the cell medium of one plate and a similar amount of only the carrier of the drug, for example ethanol 10 μl, to another plate. After 48 to 74 hours, the cell density in control (ethanol) and experimental (clotrimazole) plates is assessed under a light inverted microscope, by measuring the surface of the culture plate covered by the cell monolayer. Alternatively, the cells can be detached from the plate by incubation with trypsin (Sigma, Co.) 50% (v/v) in ethylene diaminotetraacetic acid (ECTA; Sigma, Co); then the cells are counted in an hemocytometer chamber (Fisher, Pittsburgh, Pa.).

Assays for Inhibitors of $Ca^{++}$ Activated K Channel $Ca^{++}$-sensitive $K+$ channels have wide distribution among cells, including the human red cell where they were originally discovered and which is the most commonly utilized assay system for activators and inhibitors of the channel for the following reasons: they are readily available, can be easily manipulated in the laboratory, and transport assays can be accurately standardized by reading the hemoglobin concentration of a red cell suspension.

Preparation of Human Red Blood Cells: Blood is collected in heparinized tubes and centrifuged in a Sorvall centrifuge (RB 5B, Du Pont Instruments, Newtown, Conn.) at 5° C. for 10 minutes at 3000 g. Plasma and buffy coat are carefully removed and the cells washed four times with a washing solution containing 150 mM choline chloride (Sigma Co), 1 mM MgCl2 (Sigma Co), 10 mM Tris-MOPS (Sigma, Ca), pH 7.4 at 4° C.(CWS). An aliquot of cells is then suspended in an approximately equal volume of CWS, and from this original cell suspension hematocrit (Hct) and hemoglobin (optical density at 540 nm) are determined.

Methods to Test Inhibitors of the $Ca^{++}$ Activated K: To test inhibitors of the $Ca^{++}$ activated K channel, the channel is activated using the calcium ionophore A23187 (Chalbiochem).

By Atomic Absorption Spectrometry: Washed human erythrocyte are suspended at an hematocrit =1% in CWS containing 0.150 mM CaCl2 (Sigma Co) Aliquots of 1 ml are removed at 0, 3 and 5 minutes, layered on top of 0.3 ml of the oil n-butyl phthalate (Fair Lane, N.J.) placed in an Eppendorf microtube (Fisher) and then centrifuged in a micro centrifuge for 20 seconds. At time 5.30 minutes, ionophore A23187 (1 μM final concentration) is added and samples removed and spin down through phthalate at times 6, 7, 8 and 9 minutes. The supernatant on top of the oil layer is removed and its $K+$ concentration is measured by atomic absorption spectrometry using a Perking Elmer model 5000 spectrometer (Perkin Elmer Corp., Norwolk, Conn.). The efflux of $K+$ (mmol/1 cells/h) in the absence and presence of the inhibitor is calculated from the slope of the curves relating the $K+$ concentration in the supernatants (mmol/1 cells) vs. time (min.).

By radioisotopic measurement of $^{86}Rb$ influx. The incubation medium is the same but contains 2 mM KCl and 1 μCi/ml of the radioactive tracer $^{86}Rb$. After spinning the samples through the phthalate layer, the tubes are rapidly frozen (−80° C.) by immersion in methanol-dry ice, the tips of the tubes containing the packed red cells cut, and counted in a Packard Gamma Counter.

Example 1

The inhibitory effect of clotrimazole (CLT) on cell proliferation was assessed in normal, non-cancerous cells.

Rat vascular smooth muscle cells (murine cell line): Quiescent cells were stimulated with purified growth factors (PDGF and bFGF, 5 μM) and synthesis of DNA was assessed by the incorporation of [3H]thymidine measured 24 hours later. As shown in FIG. 1, 10 μM CLT completely inhibited both PDGF and bFGF stimulated DNA synthesis. The effect was not due to a toxic, non-specific, effect because it was reversed by removing CLT and re-stimulating the cells with the corresponding growth factor (FIG. 1).

Example 2

Figure 2:
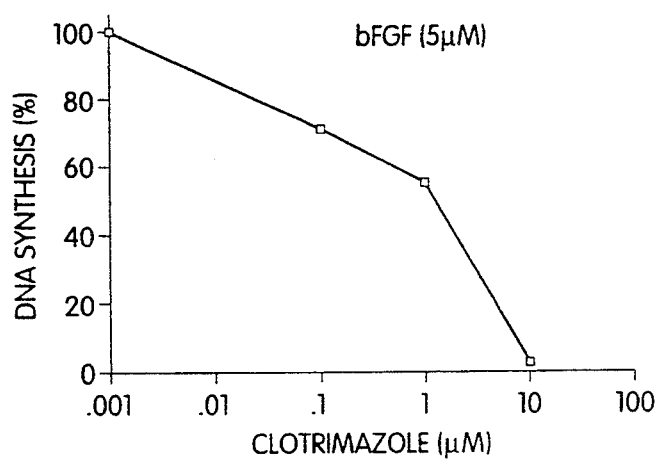
FIG. 2 is a graph showing that clotrimazole inhibits DNA synthesis in a dose-dependent fashion.

Dose response inhibitors of DNA synthesis by clotrimazole was tested using rat vascular smooth muscle cells as described above. Clotrimazole was tested at concentrations of 0.001 μM, 0.1 μM, 1 μM and 10 μM. Cells were stimulated using 5 μM bFGF. Inhibition was dose dependent, with 45% inhibition at 1 μM and complete inhibition at 10 μM. The $ID_{50}$ was about 1.5 μM. (FIG. 2)

Example 3

Bovine endothelial (BAEC) and human umbilical vein (HUVEC): Cells were seeded at a low density ($2.5 \times 10^5$) in cell culture flasks (75 ml flasks) containing DME 10% calf serum (BAEC) or fetal calf serum (HUVEC) after 12 hs, when the cells were attached to the surface of the flasks, CLT (10 μM) or carrier (ethanol) were added to triplicate flasks. After 48 hs cell growth was assessed by optic miscroscopy calculating the surface of the culture flask covered by the cell monolayer. Both BAEC and HUVEC cells had covered 90±2% of the flask surface in the absence and less than 10% in the presence of CLT (data not shown).

Example 4

Figure 3:
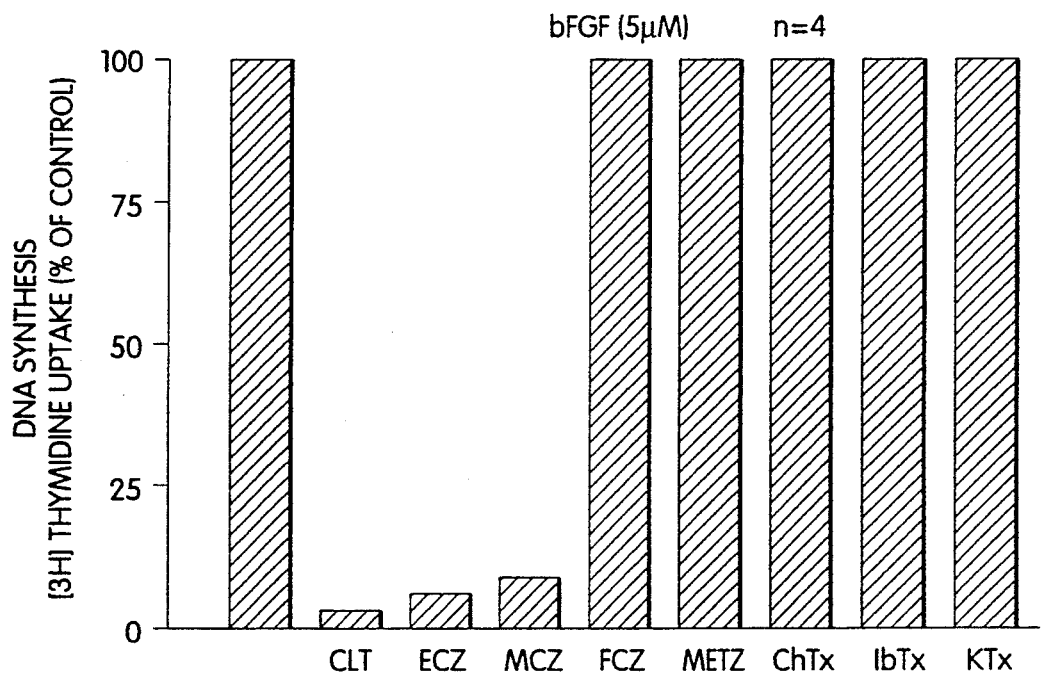
FIG. 3 is a graph comparing the effect upon cell proliferation of a variety of drugs.

Other antimycotics were tested for their inhibition of bFGF-stimulated DNA synthesis in rat vascular smooth muscle cells. As shown in FIG. 3, at a concentration of 10 μM, 3 compounds, CLT, econazole (ECZ) and miconazole (MCZ) inhibited DNA synthesis. The order of inhibitory potency was CLT more potent than ECZ, and ECZ more potent than MCZ. In contrast, other inhibitors of the $Ca^{++}$ activated K channel, namely Charybdotoxin, kaliotoxin and iberotoxin, also failed to inhibit DNA synthesis.

Example 5

The inhibitory effect of (CLT) on the $Ca^{++}$ activated K channel of human erythrocytes was assessed in the presence of 60 μmol A23187/L cell and 100 μMCaCl$_2$. CLT markedly inhibited the $CA^{++}$ activated 86Rb influx and K efflux. Mean values of $ID_{50}$ (calculated with Dixon plot analysis) was 143±60 nM(n=3).

Figure 4:
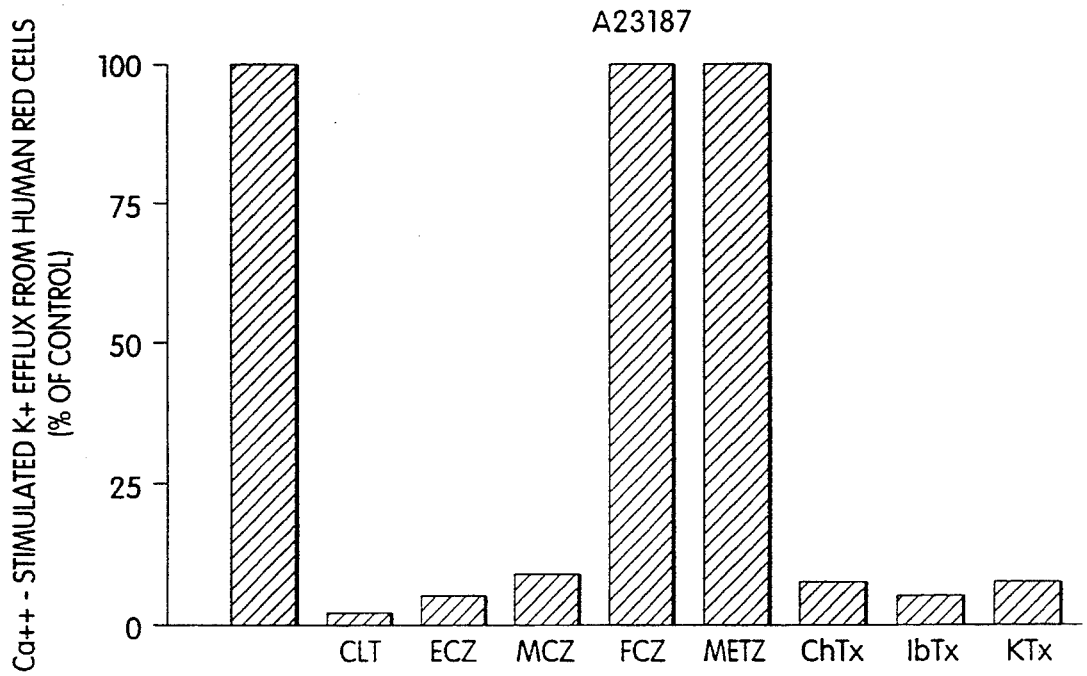
FIG. 4 is a graph comparing the effect upon the $Ca^{++}$ activated potassium channel of the same drugs tested in connection with FIG. 3.

Other antimycotics were tested for their inhibition of the $Ca^{++}$ activated 86Rb influx human erythrocytes. The order of inhibitory potency was clotrimazole more than miconazole; and both of these were more than econazole. There was no inhibition by fluconazole, ornidazole and tinidazole, 2 related compounds, and only marginal with metronidazole a member of the nitroimidazole group (FIG. 4).

Example 6

CLT inhibits the mitogenic activity released from endothelial cells by activated complement. When endothelial cells (EC) in culture (both BAEC and HUVEC) are treated with terminal complement components to form the MAC (membrane attack complex of complement), they release into the culture medium a potent mitogenic activity that stimulates the proliferation of quiescent cells used as indicators of the mitogens. Both, quiescent Swiss 3T3 and vascular smooth muscle cells are stimulated by the mitogens released form EC in response to the MAC (FIG. 5; Halperin et al. unpublished observation). Moreover, immunoprecipitation with specific antibodies has documented that both PDGF and bFGF released from the EC contribute in approximately equal proportion to the mitogenic activity induced by the MAC (data not shown).

Figure 5:
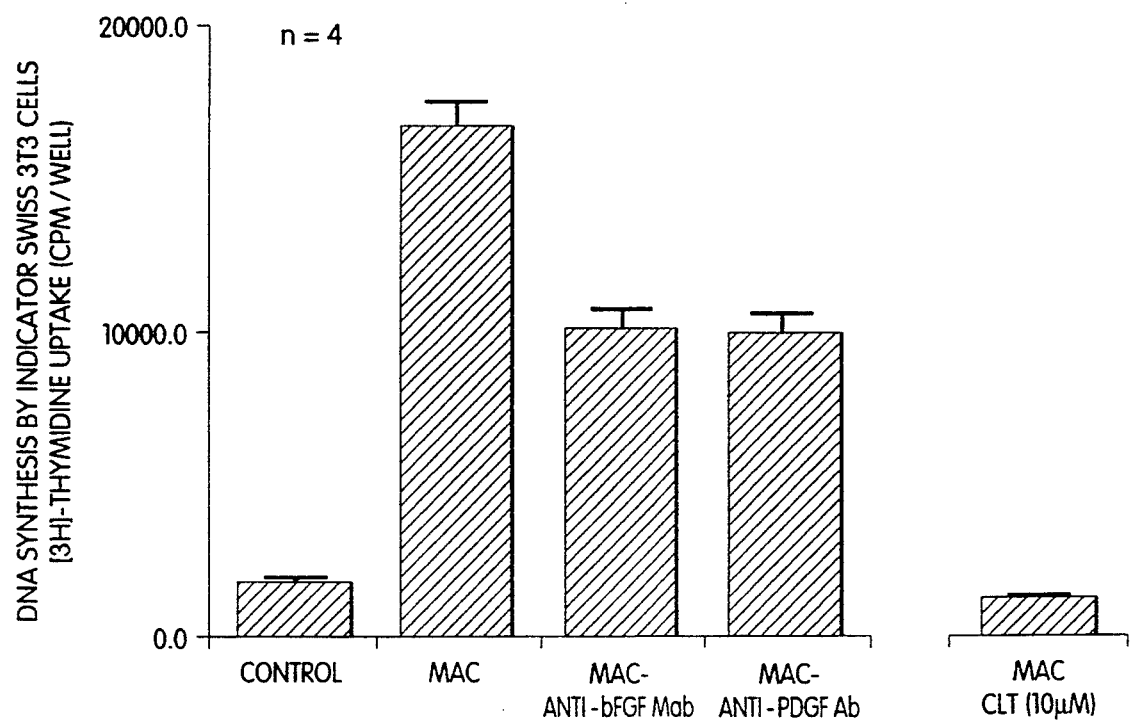
FIG. 5 is a graph illustrating the inhibitory effect that clotrimazole has upon complement-induced release of mitogenic activity from endothelial cells.

To determine whether CLT inhibited the cell proliferative activity released by the MAC from EC, quiescent 3T3 and vascular smooth muscle cells were stimulated in the presence and absence of 10 μM CLT with conditioned media obtained from MAC treated EC. The results indicate that CLT completely inhibited the proliferative response to mitogens released from EC (FIG. 5).

Example 7

The inhibitory effect of clotrimazole (CLT) on cell proliferation was assessed in normal fibroblasts.

Swiss 3T3 cells (murine fibroblast cell line): Quiescent cells were stimulated with purified growth factors (PDGF and bFGF, 5 μM) and synthesis of DNA was assessed by the incorporation of [3H]thymidine measured 24 hours later. 10 μM CLT completely inhibited both PDGF and bFGF stimulated DNA synthesis. The effect was not due to a toxic, non-specific, effect because it was reversed by removing CLT and re-stimulating the cells with the corresponding growth factor.

Those skilled in the art will be able to ascertain with no more than routine experimentation numerous equivalents to the specific imidazoles and processes described herein. Such equivalents are considered to be within the scope of the invention and are intended to be embraced by the following claims in which we claim:

1. A method for treating an arteriosclerotic condition, comprising:
   administering to a subject in need of such treatment an imidazole selected from the group consisting of: chlotrimazole, miconazole, econazole and their pharmaceutically acceptable salts.

2. A method for treating an arteriosclerotic condition as claimed in claim 1 wherein the imidazole is administered to a subject who has sustained an injury to a blood vessel.

3. A method for treating an arteriosclerotic condition as claimed in claim 2 wherein the imidazole is administered to a subject who has undergone a balloon angioplasty procedure to prevent restenosis in the subject.

4. A method for treating an arteriosclerotic condition as claimed in claim 2 wherein the imidazole is administered to a subject who has undergone vascular surgery.

5. A method for treating an arteriosclerotic condition as claimed in claim 1 wherein the imidazole is administered to a subject who has undergone a heart transplant.

6. A method for treating an arteriosclerotic condition as claimed in claim 1 wherein the imidazole is administered to a subject who has classical atherosclerosis.

7. A method for treating an arteriosclerotic condition as claimed in claim 1 wherein the imidazole is administered to a subject who has diabetes.

8. A method for treating an arteriosclerotic condition as claimed in any one of claims 1, 2, 3, 4, 5, 6 and 7, wherein clotrimazole is administered to the subject.

9. A method for treating an arteriosclerotic condition as claimed in any one of claims 1, 2, 3, 4, 5, 6 and 7, wherein miconazole is administered to the subject.

10. A method for treating an arteriosclerotic condition as claimed in any one of claims 1, 2, 3, 4, 5, 6 and 7, wherein econazole is administered to the subject.

11. A method for inhibiting vascular smooth muscle cell proliferation comprising contacting vascular smooth muscle cells of a species with an imidazole selected from the group consisting of: clotrimazole, miconazole, econazole and their pharmaceutically acceptable salts.

12. A method for inhibiting smooth muscle cell proliferation as claimed in claim 11, wherein the muscle cells are contacted with the imidazole ex vivo.

13. A method for inhibiting smooth muscle cell proliferation as claimed in claim 11 wherein the muscle cells are free of fungus.

14. A method for inhibiting endothelial cell proliferation comprising contacting endothelial cells of a species with an imidazole selected from the group consisting of: clotrimazole, miconazole, econazole and their pharmaceutically acceptable salts.

15. A method for inhibiting endothelial cells proliferation as claimed in claim 14 wherein the endothelial cells are contracted with the imidazole ex vivo.

16. A method for inhibiting endothelial cell proliferation as claimed in claim 14 wherein the endothelial cells are free of fungus.

17. A method for inhibiting fibroblast proliferation comprising contacting fibroblasts of a species with an imidazole selected from the group consisting of: clotrimazole, miconazole, econazole and their pharmaceutically acceptable salts.

18. A method for inhibiting fibroblast proliferation as claimed in claim 17 wherein the fibroblasts are contracted with the imidazole ex vivo.

19. A method for inhibiting fibroblast proliferation as claimed in claim 17 wherein the fibroblasts are free of fungus.

20. A method for treating an arteriosclerotic condition as claimed in any one of claims 1, 2, 3, 4, 5, 6 and 7, wherein econazole nitrate is administered to the subject.

21. A method for treating an arteriosclerotic condition as claimed in any one of claims 1, 2, 3, 4, 5, 6 and 7, wherein miconazole nitrate is administered to the subject.

* * * * *